(12) United States Patent
Zechiedrich et al.

(10) Patent No.: US 7,622,252 B2
(45) Date of Patent: Nov. 24, 2009

(54) GENERATION OF MINICIRCLE DNA WITH PHYSIOLOGICAL SUPERCOILING

(75) Inventors: E. Lynn Zechiedrich, Houston, TX (US); Jonathan Fogg, Houston, TX (US); John Perona, Goleta, CA (US)

(73) Assignees: Baylor College of Medicine, Houston, TX (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 11/448,590

(22) Filed: Jun. 7, 2006

(65) Prior Publication Data
US 2007/0020659 A1    Jan. 25, 2007

Related U.S. Application Data

(60) Provisional application No. 60/689,298, filed on Jun. 10, 2005.

(51) Int. Cl.
C12Q 1/68     (2006.01)
C07H 21/04    (2006.01)

(52) U.S. Cl. .......................................... 435/6; 536/23.1
(58) Field of Classification Search .................. 435/6; 530/350; 536/23.1
See application file for complete search history.

(56) References Cited

U.S. PATENT DOCUMENTS

| 6,964,861 B1* | 11/2005 | Gerard et al. | 435/91.1 |
| 2006/0211117 A1* | 9/2006 | Bigger et al. | 435/483 |

FOREIGN PATENT DOCUMENTS

| WO | WO 9409127 A2 | 4/1994 |
| WO | WO 0246372 A1 | 6/2002 |
| WO | WO 0283889 A2 | 10/2002 |
| WO | WO 0364623 A2 | 8/2003 |
| WO | WO 03103600 A2 | 12/2003 |

OTHER PUBLICATIONS

Adams et al., "The Role of Topoisomerase IV in Paritioning Bacterial Replicons and the Structure of Catenated Intermediates in DNA Replication," Cell, 1992, vol. 71, pp. 277-288.*
Darquet et al., "Minicircle: an improved DNA molecule for in vitro and in vivo gene transfer," Gene Therapy, 1999, vol. 6, pp. 209-218.*
Zechiedrich, et al., "Topoisomerase IV, not gyrase, decatenates products of site-specific recombination in *Escherichia coli*," Genes and Dev., 1997, vol. 11, pp. 2580-2592.*
Bliska et al., "Use of Site-specific Recombination as a Probe of DNA Structure and Metabolism in Vivo," J.Mol.Biol., 1987, vol. 194, pp. 205-218.*
Darquet, AM et al. Minicircle: an improved DNA molecule for in vitro and in vivo gene transfer. Gene Therapy, vol. 6, pp. 209-218, 1999.*
Napoli, A et al. A novel member of the bacterial-archeal regulator family is a nonspecific DNA binding-protein and induces positive supercoiling. J. Biol. Chem., vol. 276, No. 14, pp. 10745-10752, 2001.*
Deibler, RW et al. Topoisomerase IV, alone, unkots DNA in *E.coli*. Genes and Development, vol. 15(6), pp. 748-761, 2001.*
Andersen, A. et al., "Strand specificity of the topoisomerase II mediated double-stranded DNA cleavage reaction," *Biochemistry*, 28(15):6237-44 (1989).
Bliska, J. and Cozzarelli, N., "Use of Site-specific Recombination as a Probe of DNA Structure and Metabolism in Vivo," *J. Mol. Biol.*, 194:205-218 (1987).
Brown, P.O. and N. R. Cozzarelli, "A Sign Inversion Mechanism for Enzymatic Supercoiling of DNA," *Science* 206:1081-1083 (1979).
Corbett, A. et al., "A Two-Site Model for Enzyme-Mediated DNA Cleavage," *J. Biol.Chem.*, 267(2):683-686 (1992).
Déclais, A. et al., "The complex between a four-way DNA junction and T7 endonuclease I," *The EMBO Journal*, 22(6):1398-1409 (2003).
Fogg, J. et al., "Yeast resolving enzyme CCE1 makes sequential cleavages in DNA junctions within the lifetime of the complex," *Biochemistry*, 39(14):4082-9 (2000).
Fogg, J. et al., "Sequence and functional-group specificity for cleavage of DNA junctions by RuvC of *Escherichia coli*," Biochemistry, 38(35):11349-58 (1999).
Hamiche, A. and Prunell, A., "Chromatin reconstitution on small DNA rings. V. DNA thermal flexibility of single nucleosomes," *J. Mol. Biol.*, 228(2):327-37 (1992).
Hiller, D. et al., "Simultaneous DNA binding and bending by EcoRV endonuclease observed by real-time fluorescence," *Biochemistry*, 42(49):14375-85 (2003).
Khodursky, A. et al., "Topoisomerase IV is a target of quinolones in *Escherichia coli*," *Proc. Natl. Acad. Sci. USA*, 92, pp. 11801-11805 (1995).
Kvaratskhelia, M. et al., "Holliday Junction Resolution Is Modulated by Archaeal Chromatin Components in Vitro," *J. Biol. Chem.*, 277(4):2992-2996 (2002).
Liu, Z. et al., "Topological information embodied in local juxtaposition geometry provides a statistical mechanical basis for unknotting by type-2 DNA topoisomerases," *J. Mol. Biol.*, 361(2):268-85 (2006).
Liu, Z. et al., "Inferring global topology from local juxtaposition geometry: interlinking polymer rights and ramifications for topoisomerase action," *Biophys J.*, 90(7):2344-55 (2006).
Lopez, C. et al., "A role for topoisomerase III in a recombination pathway alternative to RuvABC," *Mol. Microbiol.*, 58(I):80-101 (2005).
Osheroff, N., "Effect of antineoplastic agents on the DNA cleavage/religation reaction of eukaryotic topoisomerase II: inhibition of DNA religation by etoposide," *Biochemistry*, 28(15):6157-60 (1989).
Stasiak, A., et al., "Electrophoretic Mobility of DNA Knots," *Nature*, 384:122 (1996).
Tolmachov, O. et al., "RecET driven chromosomal gene targeting to generate a RecA deficient *Escherichia coli* strain for Cre mediated production of minicircle DNA," *BMC Biotechnol.*, 6:17 (2006).
Vaysse, L. et al., "Nuclear-targeted minicircle to enhance gene transfer with non-viral vectors in vitro and in vivo," *J. Gene Med.*, 8(6):754-63.

(Continued)

*Primary Examiner*—Suryaprabha Chunduru
(74) *Attorney, Agent, or Firm*—Hamilton, Brook, Smith & Reynolds, P.C.

(57) ABSTRACT

Methods for the production of supercoiled DNA minicircles and their use as substrates are described herein.

16 Claims, 11 Drawing Sheets

OTHER PUBLICATIONS

Wasserman, S.A. and N.R. Cozzarelli, "Biochemical Topology: Applications to DNA Recombination and Replication," *Science*, 232:951-960 (1986).

Zechiedrich, E. et al., "Double-stranded DNA cleavage/religation reaction of eukaryotic topoisomerase II: evidence for a nicked DNA intermediate," *Biochemistry*, 28(15):6229-36.

Zechiedrich, E. et al., "Roles of topoisomerases in maintaining steady-state DNA supercoiling in *Escherichia coli*," *J. Biol. Chem.*, 275(11):8103-13 (2000).

Zechiedrich, E. et al., "Topoisomerase IV, not gyrase, decatenates products of site-specific recombination in *Escherichia coli*," *Genes & Development*, 11:2580-2592 (1997).

Bates, A.D. and Maxwell, A., "DNA Topology," Oxford University Press:NY, pp. 25-31, 38-39, 107-115 (2005).

Burnier, Y. et al., "DNA Supercoiling Inhibits DNA Knotting," *Nucleic Acids Research*, 36(15):4956-4963 (2008).

Lewin, B., "Genes VI," Oxford University Press: NY, pp. 109-112 & 550-554 (1997).

\* cited by examiner

US 7,622,252 B2

GENERATION OF MINICIRCLE DNA WITH PHYSIOLOGICAL SUPERCOILING

RELATED APPLICATION

This application claims the benefit of U.S. Provisional Application No. 60/689,298, filed Jun. 10, 2005.

The entire teachings of the above application are incorporated herein by reference.

GOVERNMENT SUPPORT

The invention was supported, in whole or in part, by grants AI054830 and GM53763 from the National Institutes of Health and MCB-0090880 from the National Science Foundation. The Government has certain rights in the invention.

BACKGROUND OF THE INVENTION

DNA supercoiling affects almost all processes involving DNA in vivo. DNA topology affects cellular processes such as, for example, transcription, replication, packaging and segregation. Although the effects of DNA topology lead to significant alterations in cellular processes, much of the research devoted to understanding these processes is performed in vitro on substrates that do not adequately approximate physiological topology. For example, proteins that bind DNA ("DNA binding proteins") often have different affinities and/or kinetics for DNA depending on the degree to which the DNA is supercoiled. Studying DNA binding by these proteins on substrates that do not approximate physiological topology is an inherent disadvantage with the DNA substrates used in these studies.

The use of DNA minicircles, for example, in binding studies has been suggested, but they have been difficult to produce and purify in significant quantity. DNA minicircles lack an origin of replication and are typically lost during cell division. However, if DNA minicircles are synthesized as linear molecules and then circularized by in vitro ligation, they do not exhibit physiological topology. When such minicircles pass through the linear stage, they lose their superhelicity. As only closed minicircles are topologically constrained, linear molecules must be ligated to form minicircles. However, yields are low and intermolecular ligation contaminants are prevalent when the short linear DNA molecules necessary for generating minicircles are used. Alternatively, without an origin of replication, such circles are not efficiently produced in large quantities in vivo.

Although there is promise for the use of minicircles for in vitro studies of DNA, e.g., for DNA binding assays, their use as a substrate is limited by their difficulty to be produce in large quantities while retaining a physiological topology.

SUMMARY OF THE INVENTION

The present invention discloses methods for producing supercoiled DNA minicircles and their use as substrates that interact with proteins. As described herein, it is an unexpected discovery that inhibition of topoisomerase IV results in the in vivo production of supercoiled minicircles in quantities (e.g. milligram quantities) greater than could be previously achieved. Also described herein are methods for using the supercoiled DNA minicircles for screening for agents that disrupt protein-DNA interactions and their use in other genomic and proteomic studies.

In one embodiment, the invention is directed to a method for producing supercoiled DNA minicircles, comprising a) engineering a plasmid DNA molecule comprising site-specific recombination sites; b) transforming the plasmid into a cell suitable for site-specific recombination to occur, under conditions such that topoisomerase IV decatenation activity is inhibited, thereby producing a plurality of catenated DNA circles, wherein at least one of the circles in each catenane is a supercoiled DNA minicircle; and c) recovering the supercoiled DNA minicircles from the cell. In a particular embodiment, the catenated site-specific recombination products are decatenated by a site-specific endonuclease that cleaves only the larger catenated DNA circles. In one embodiment, supercoiled DNA minicircles are separated from nicked DNA minicircles. In a particular embodiment, the site-specific recombination sites are selected from the group consisting of: attB, attP, loxP sites, γδ res sites, FRT sites, hixL, hixR, TN3 res sites, Tn21 res sites, psi sites and cer sites, and wherein the site-specific recombination reaction utilizes an enzyme selected from the group consisting of: γε resolvase, Hin recombinase, P1 Cre, yeast 2 micron Flp, Tn3 resolvase, Tn21 resolvase, γ integrase and XerCD.

In one embodiment, topoisomers of the supercoiled minicircles are separated from each other, thereby producing substantially purified DNA minicircles, wherein the DNA minicircles have the same linking number. In a particular embodiment, the DNA minicircles have a ΔLk of between about +6 to about −6, and more particularly, of between about −1 to about −6. In one embodiment, the site-specific recombination sites are separated by about 100 base pairs to about 1000 base pairs, and more particularly, about 250 base pairs to about 1000 base pairs. In a specific embodiment, the site-specific recombination sites are separated by about 342 base pairs.

In another embodiment, the invention is directed to an isolated supercoiled DNA minicircle. In another embodiment, the minicircle comprises an engineered protein binding site, wherein the protein binding site is an actual or putative binding site for a protein of interest. In a particular embodiment, the one or more proteins of interest are selected from the group consisting of: topoisomerases, site-specific recombinases, restriction endonucleases, transcription factors, remodeling factors, DNA bending proteins, helicases, polymerases and DNA repair proteins.

In another embodiment, the invention is directed to a method for producing a population of supercoiled DNA minicircles, comprising a) engineering a plasmid DNA molecule comprising site-specific recombination sites; b) transforming the plasmid into a cell suitable for site-specific recombination to occur, under conditions such that topoisomerase IV decatenation activity is inhibited, thereby producing a plurality of catenated DNA circles, wherein at least one of the circles in each catenane is a supercoiled DNA minicircle; c) recovering the supercoiled DNA minicircles from the cell; d) treating the supercoiled DNA minicircles with an enzyme that introduces nicks into the DNA minicircle; and e) ligating the nicked minicircle in the presence of a DNA intercalator that introduces supercoils, thereby producing a population of supercoiled DNA minicircles. In a particular embodiment, the enzyme that introduces nicks into the DNA minicircle is a nicking endonuclease. In one embodiment, the DNA intercalator is ethidium bromide.

In yet another embodiment, the invention is directed to a method for producing a population of supercoiled DNA minicircles, comprising a) engineering a plasmid DNA molecule comprising site-specific recombination elements; b) transforming the plasmid into a cell suitable for site-specific recombination to occur under conditions such that topoisomerase IV is inhibited, thereby producing a plurality of catenated DNA circles; c) isolating the catenated circles of b), wherein at least one of the circles in each catenane is a nicked DNA minicircle; d) decatenating the site-specific recombination products with an endonuclease, thereby producing large linear DNA fragments and nicked DNA minicircles; e) purifying the nicked DNA minicircles; and f) treating the nicked DNA minicircles with one or more intercalators and a suitable DNA ligase, thereby creating supercoiled minicircles without nicks. In a particular embodiment, the catenated site-specific recombination products are decatenated by a site-specific endonuclease that cleaves only the larger catenated DNA circles. In one embodiment, supercoiled DNA minicircles are separated from the nicked DNA minicircles prior to treating the nicked DNA minicircles with one or more intercalators.

In another embodiment, the invention is directed to a method for identifying DNA binding proteins, comprising a) isolating a supercoiled DNA minicircle comprising a putative DNA binding site; b) contacting the supercoiled DNA minicircle with a protein of interest under conditions suitable for DNA binding; and c) assaying for DNA binding, wherein DNA binding is indicative of a DNA binding protein.

In yet another embodiment, the invention is directed to a method for screening for modulators of DNA binding proteins, comprising a) contacting a DNA binding protein of interest with a supercoiled DNA minicircle under conditions suitable for DNA binding in the presence and absence of a test agent; and b) quantifying the amount of DNA binding in the presence and absence of the test agent, wherein altered DNA binding is indicative of the test agent's being a modulator of DNA binding.

In one embodiment, the supercoiled DNA minicircle can be attached to a solid support.

DETAILED DESCRIPTION OF THE INVENTION

Figure 1:
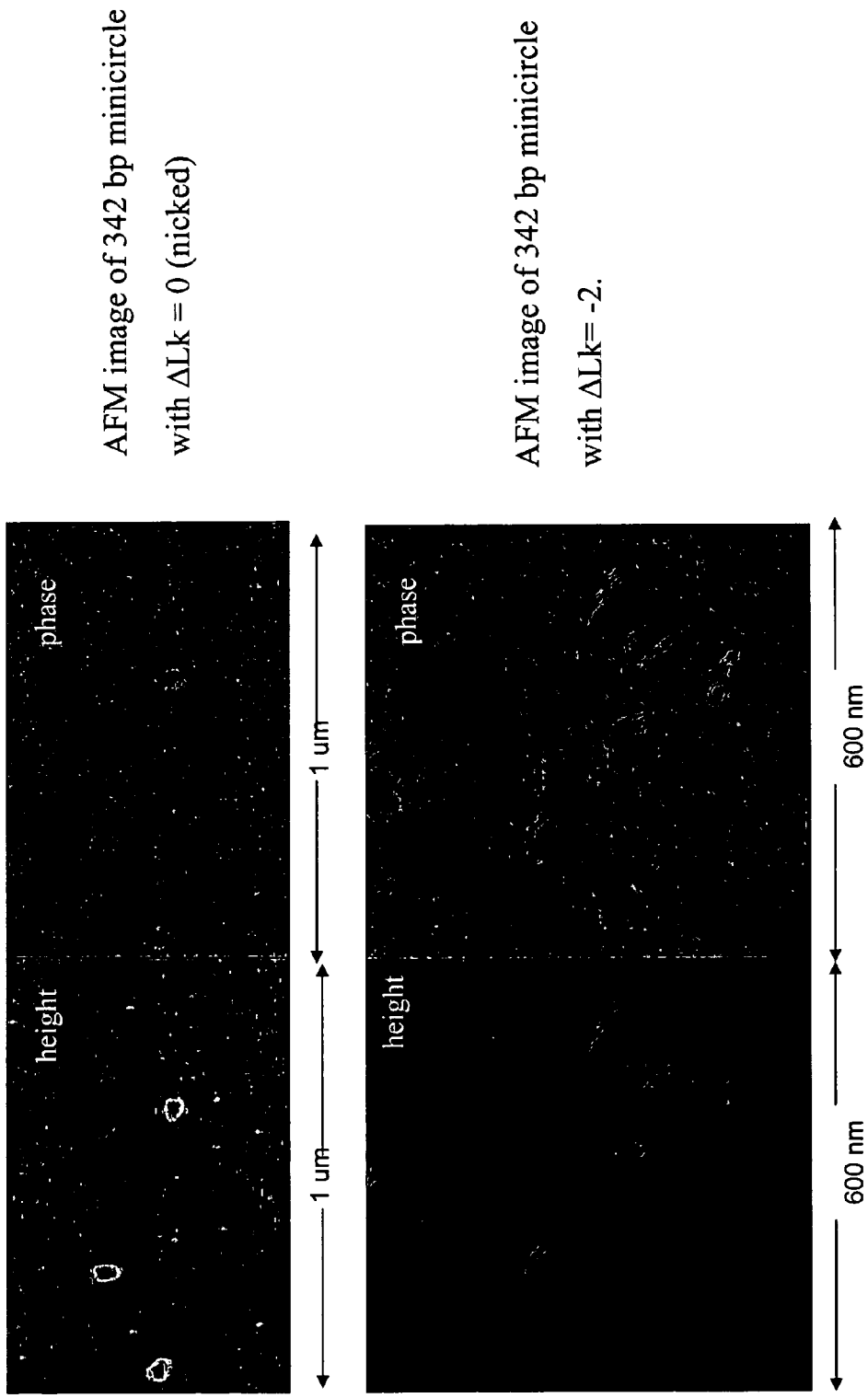
FIG. 1 is an atomic force microscopy (AFM) image depicting "relaxed" ($\Delta Lk=0$) minicircles and "supercoiled" ($\Delta Lk=-2$) DNA minicircles.

Disclosed herein is a method for the production and isolation of large quantities of supercoiled minicircle DNA substrates with well-defined supercoiling levels (see FIG. 1). A DNA minicircle is a double-stranded, circular DNA molecule of less than about 1 kb in size, and, preferably, between about 100 base pairs and 1 kb in size. The DNA minicircles described herein have a well-defined topology and are isolated in populations comprising a single topoisomer. Due to their size, DNA minicircles do not contain a selectable marker or origin of replication.

In a particular embodiment, supercoiled DNA minicircles are generated by in vivo site-specific recombination, although site-specific recombination can be performed in vitro using purified components. Site-specific recombination systems that result in catenated circles have been well-characterized in the art, and can be used in a variety of host cells such as, for example, bacteria, yeast and mammalian cells in culture. One of skill in the art would select a suitable recombination system and host cell according to the nature and quantity of supercoiled minicircle to be produced. The method for generating DNA minicircles relies on site-specific recombinases, e.g., γδ resolvase, Hin recombinase, P1 Cre, yeast 2 micron Flp, Tn3 resolvase, Tn21 resolvase, γ integrase and XerCD. Recombinases are enzymes that beak and rejoin double-stranded DNA (dsDNA) at specific sequence elements. Although specific examples are described using γ integrase, the methods of the present invention encompasses the use of any enzyme capable of producing catenated recombination products as a result of site-specific recombination.

As disclosed herein, two site-specific recombination sites are incorporated into a plasmid. Recombination between the two sites results in the conversion of the plasmid into two catenated rings: one large ring and a minicircle. Cells have an enzyme that decatenates such products (a "decatenation activity"). Normally in *Escherichia coli* (*E. coli*), such catenated DNA circles are decatenated by the action of topoisomerase IV. Described herein are methods for producing catenated products under conditions such that a cell's decatenation activity, e.g., the activity of topoisomerase IV, is inhibited. Because the plasmid contains elements for selection and replication during cell division, the minicircle is amplified and retained by cells during cell division. Thus, the minicircle, as a part of the overall plasmid is produced in large quantities. Minicircles on their own would typically be lost during cell division because they lack selectable markers and an origin of replication. The present invention allows for the overproduction, in milligram quantities, of supercoiled minicircle DNA with a size range of between about 250 base pairs and about 1000 base pairs. The yields are one to two orders of magnitude greater than previously obtainable. The major advantages of using supercoiled DNA minicircles compared to large plasmids are that (i) they adopt highly constrained topoisomer distributions, (ii) the superhelical density can be set precisely, (iii) they can be used in quantitative gel mobility shift assays, (iv) the large yields now achievable, and the small size of the minicircle, open up the possibility of crystallizing these substrates as complexes with DNA-binding proteins.

Figure 2:
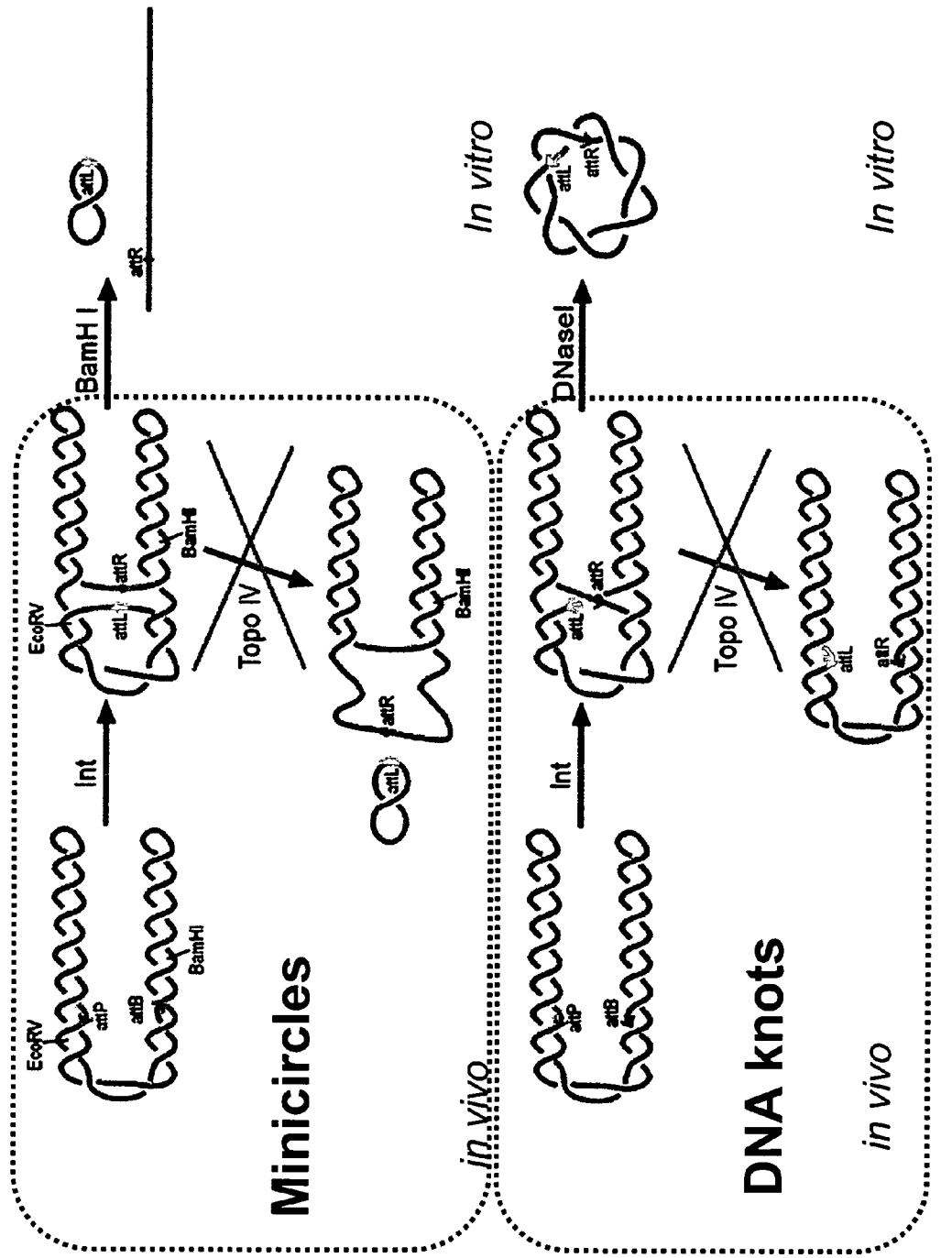
FIG. 2 is a schematic diagram illustrating site-specific recombination and possible site-specific recombination products.

Supercoiled DNA minicircles are created through site-specific recombination reactions (sometimes referred to as non-homologous recombination). These reactions are facilitated by enzymes (e.g., recombinases, integrases, resolvases, etc). These enzymes promote two double-stranded DNA (dsDNA) cleavage reactions and two strand transfer reactions. The strand cleavage reactions occur at specific sites, herein referred to generally as "recombination sites" including, for example, res sites for resolvases and att sites for integrases such as, for example, γ integrase. The subsequent strand transfer reaction determines the type of recombination product (see FIG. 2). For γ integrase, if the recombination sites (attB and attP) are in the same orientation, a catenated C (joined together not covalently, but rather like the links of a chain are interconnected) product results with two circular DNA molecules intertwined. If the attachment sites are in opposite orientation, an inversion occurs maintaining a single circular DNA molecule. The present invention discloses the use of substrate plasmids that will result in a catenated product comprising a large DNA circle containing the origin of replication and a smaller minicircle of about between 250 base pairs and 1000 base pairs that lacks an origin of replication.

An important feature of site-specific recombinases is that they bind to specific recombination sites and remain bound after cleavage and during strand transfer. Since closed circular DNA molecules are topologically constrained, if the original substrate DNA is supercoiled, the superhelicity is maintained during recombination due to the constantly bound recombinase. "Nicks" (single-stranded cuts in DNA) or double-stranded breaks will release these topological constraints (change the linking number, see below). The release of topological constraints is referred to as "relaxing" or "unwinding". The fact that the recombinase remains bound to the cleaved DNA ends does not permit the DNA molecule to relax even though a double-strand break occurs. Therefore, supercoils are "trapped" in the substrate during cleavage and strand transfer, and the resulting catenated product retains the superhelicity of the starting substrate.

The geometry and topology of DNA can be described by three parameters. Linking number (Lk) is a topological property defined for closed, circular dsDNA. For dsDNA, Lk is the number of times two closed strands are linked or the number of times that one DNA strand winds around another. Rigorously, the linking number can be determined from the crossovers of the two DNA curves when projected onto a plane. Lk is computed by first taking a planar projection of the 2 orientated curves, assigning signs to the crossings between the 2 curves, and computing half the sum of these signs. It is impossible to change the linking number of a plasmid without breaking a covalent bond (without breaking one strand, passing the second strand through the break and rejoining the break). Thus, linking number is a topological invariant. The linking number of the relaxed state of a closed, circular DNA molecule is approximately equal to the number (N) of base pairs divided by 10.5, the period of the helix. This is an approximation because N/10.5 need not be an integer, but linking number is by definition an integer.

The linking difference, or $\Delta Lk$, is the difference between the linking number, Lk, of the current DNA state of the DNA molecule of interest and the linking number, $Lk_0$, of the relaxed state of that same DNA molecule. That is, $\Delta Lk = Lk - Lk_0$ Whenever $\Delta Lk$ is nonzero the DNA is said to be "super-coiled". Positive $\Delta Lk$ corresponds to $Lk > Lk_0$, which occurs in the case of positively supercoiled DNA; negative $\Delta Lk$ corresponds to $Lk < Lk_0$, which occurs in the case of negatively supercoiled DNA.

Changes in the linking number are accommodated either by over- or under-winding of the DNA helix (twist), or by the helix coiling upon itself (writhe). More specifically, the property twist (Tw) describes how the individual strands coil around each other along the DNA helical axis. The property writhe (Wr) describes the coiling of the helix in space. These real-valued, geometric properties of the double helix are related to the topological property linking number by the equation:

$Lk = Tw + Wr$

Any change in linking number can be manifested as a change in the twist and/or the writhe of the DNA such that:

$\Delta Lk = \Delta Tw + \Delta Wr$ $\Delta Lk$ is a real number and not a topological invariant because it depends on solution conditions.

DNA has a preferred apparent linkage number for a specified length of DNA: Watson's and Crick's model of the DNA duplex had 10 base pairs per turn. Under physiological salt conditions (0.2 M NaCl, pH=7, 37° C.), DNA prefers to adopt about 10.5 bp/turn. Therefore DNA of certain length has an inherent number of double helical turns by virtue of its structure. Thus linking number of such a DNA molecule can be approximated by:

$Lk \approx$ (size of DNA in base pairs)/(base pairs/turn)

However this value is likely to not be an integer. Where the DNA is bent into a simple, planar circle, with no writhe, the ends of the strands will not line up precisely. Where the DNA axis is restrained to lay on a plane, Lk is equivalent to Tw. A small amount of twisting is necessary to bring the ends together resulting in a linking number with an integer value. Introducing supercoiling into a DNA molecule either reduces or increases the number of helical turns.

Normally in *E. coli* the superhelical density is around −0.06 to −0.075 (see Zechiedrich, E. L. et al., 2000. *J. Biol. Chem.*, 275:8103-8113). This corresponds to a $\Delta Lk$ for the 342 bp minicircle of −2. This is, indeed, what is obtained from the in vivo preparation of the 342 bp supercoiled DNA minicircle (see Exemplification). As used herein, the term "hyper-negatively" supercoiled refers to a degree of negative supercoiling that exceeds this predicted level of supercoiling based on normal *E. coli* superhelical density (e.g., exhibiting a $\Delta Lk$ of between about −3 and about −6).

These descriptions of the geometric and topological properties of DNA are known in the art and referred to herein to describe the physiological topology achieved in the production of DNA minicircles as described herein.

DNA minicircles of the present invention are produced as a result of site-specific recombination at defined sites, called site-specific recombination sites. Although site-specific recombination sites often exhibit some complementarity, site-specific recombination does not require large regions of homology (which is why it is sometimes referred to as "non-homologous recombination"). Site-specific recombination sites for many enzymes, e.g., γδ resolvase, Hin recombinase, P1 Cre, yeast 2 micron Flp, Tn3 resolvase, Tn21 resolvase, γ integrase and XerCD, have been identified. Such sites include γδ res sites (γδ resolvase), hixL, hixR (Hin recombinase), loxP sites (P1 Cre), FRT sites (2 micron Flp), TN3 res sites, Tn21 res sites, attB and attP (γ integrase), and psi sites and cer sites (XerCD). Site-specific recombination can be performed in vivo or in vitro using purified components.

Where site-specific recombination sites are engineered into a plasmid and site-specific recombination is allowed to proceed, many possible products result, depending on how the DNA strands are cut and rejoined. These products are separable by methods known in the art, e.g., agarose gel electrophoresis, column chromatography and gel filtration. If DNA strands are cut and rejoined in a particular manner, interconnected closed circular DNA molecules are produced where a large DNA circle and a DNA minicircle are interconnected. The manner in which the circles are connected is not a chemical linkage, but rather, the two circular DNA molecules are "catenated" or linked analogous to the way links of a chain are linked. The DNA circles are separate molecules, but they are connected due to their catenated linkage. Disclosed herein are plasmids that, after site-specific recombination, lead to a catenated product where the minicircle is between about 250 base pairs to about 1000 base pairs, and the larger catenated circle contains the remainder of the original plasmid. Of note, the minicircle does not contain an origin of replication, so, if the molecules become decatenated or if two separate circles are produced as a result of the site-specific recombination reaction, the minicircle would be lost during cell division.

As described herein, the catenated DNA molecules can be nicked or cleaved during the purification process. During purification, the minicircle can become nicked, probably due to residual endonuclease activity in the cell preparation. Nicked minicircle are a byproduct of the purification procedures, but instead of being a contaminant, they can be isolated and used. In one embodiment of the invention, nicked minicircles are isolated and subsequently supercoiled by using chemical intercalators to induce supercoiling. Alternatively, catenated products can be nicked with enzymes having a nicking activity, e.g., DNase I and nicking endonuclease, such as, for example, N.BbvCIB. As mentioned above, a physical break in a DNA strand will change Lk by relaxing the DNA.

The catenanes are purified and decatenated. Decatenation is performed, for example, by treating the catenated product with a restriction endonuclease that only cleaves the larger DNA circle and not the DNA minicircle. The linearized cleaved product is separated from the supercoiled DNA minicircles by any of a number of methods known in the art, e.g., agarose gel electrophoresis, column chromatography or gel filtration.

An "isolated" nucleic acid molecule, e.g., a supercoiled DNA minicircle, as used herein, is one that is separated from other nucleic acids comprising different topologies, sizes and/or sequences that normally are present in vivo. Such isolated molecules have been completely or partially purified from these other nucleic acids. For example, an isolated nucleic acid of the invention can be substantially isolated with respect to the complex cellular milieu in which it naturally occurs, or culture medium or other purified components when produced in vitro. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography such as HPLC. An isolated nucleic acid molecule of the invention can comprise at least about 50, 80 or 90% (on a molar basis) of all macromolecular species present.

In a particular embodiment of the invention, nicked DNA minicircles are decatenated and isolated, e.g., by polyacrylamide gel electrophoresis (PAGE). Although these minicircles are relaxed due to the nick, it was unexpectedly found that these particular DNA minicircles are efficiently supercoiled by chemical intercalators known in the art to induce supercoils. Minicircles that are produced by other methods, however, exhibit a low efficiency of induced supercoils, whereas the nicked DNA minicircles isolated by the methods described herein, are efficiently supercoiled by small molecule intercalators. Examples of such intercalators include, but are not limited to, ethidium bromide (EtBr) and chloroquine. The list of potential intercalators known in the art is extensive, as many drugs have been developed that act through intercalation such as, for example, m-AMSA, daunorubicin and doxorubicin. In addition, there are a number of fluorescent DNA stains that bind through intercalation. These include, for example, EtBr, acridine orange and propidium iodine.

The isolated supercoiled minicircles can be attached to, for example, a solid support (column chromatography matrix, wall of a plate, microtiter wells, column pore glass, pins to be submerged in a solution, beads, etc.). Accordingly, in one embodiment, the supercoiled DNA minicircles can be fixed to a solid phase directly or indirectly, e.g., by a linker or other molecule. Examples of such solid supports include, but are not limited to, plastics such as polycarbonate, complex carbohydrates such as agarose and sepharose, and acrylic resins such as polyacrylamide and latex beads. Techniques for coupling nucleic acid probes to such solid supports are well known in the art.

In another embodiment of the invention, the isolated DNA minicircles are used to screen for agents that bind to DNA under physiological supercoiling conditions. The minicircles can, for example, be engineered to contain putative binding sites for DNA binding proteins. Such proteins include, but are not limited to, topoisomerases, site-specific recombinases, restriction endonucleases, transcription factors, remodeling factors, DNA bending proteins, helicases, polymerases and DNA repair proteins.

The candidate agent to be tested is added under conditions conducive for interaction and binding to the protein. The ligand is added to the solid phase system under conditions appropriate for binding. Excess ligand is removed, as by a series of washes done under conditions that do not disrupt protein-ligand interactions. Detection of bound ligand can be facilitated by using a ligand that carries a label (e.g., fluorescent, chemiluminescent, radioactive). In a control experiment, protein and ligand are allowed to interact in the absence of any candidate agent, under conditions otherwise identical to those used for the "test" conditions where candidate inhibiting agent is present, and any washes used in the test conditions are also used in the control. The extent to which ligand binds to the protein in the presence of candidate agent is compared to the extent to which ligand binds to the protein in the absence of the candidate agent. If the extent to which interaction of the protein and the ligand occurs is less in the presence of the candidate agent than in the absence of the candidate agent, the candidate agent is an agent that inhibits interaction between the protein and the ligand of the protein.

In another embodiment of the invention, the supercoiled DNA minicircles are labeled. Such labeling can occur in vivo or in vitro. For example, in vivo labeling with $^3$H thymidine allows for incorporation of $^3$H into the supercoiled minicircle final product. Alternatively, nicked or linearized minicircles can be labeled in vitro, for example, by attaching $^{32}$P with, for example, T4 polynucleotide kinase, followed by religation of the nicked or linearized minicircle in the presence of an intercalators such as, for example, ethidium bromide (EtBr). As mentioned above, isolated nicked minicircles produced by the methods described herein are efficiently ligated in the presence of intercalators to form supercoiled DNA minicircles. During ligation, intermolecular ligations do not appreciably occur, thereby allowing for efficient intramolecular ligation without contaminating intermolecular products (see Example 1).

EXEMPLIFICATION

Example 1

Site-specific recombination of a plasmid containing site-specific recombination sites can result in catenated products. Described herein is the production of such catenated products in vivo under conditions such that topoisomerase IV is inhibited, e.g., through chemical inhibitors such as, for example, norfloxacin. Also described are uses of such minicircles as substrates for proteins that act on DNA.

Figure 3:
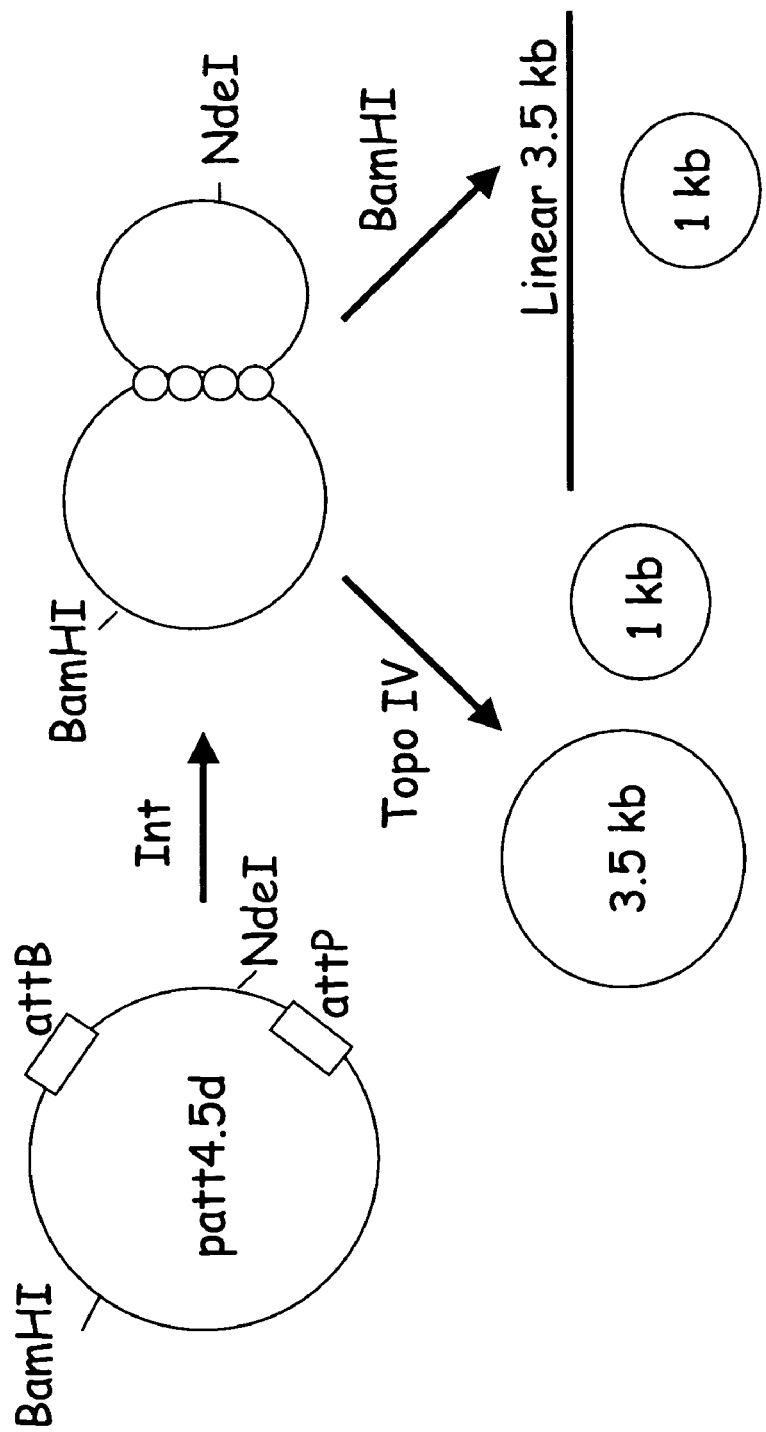
FIG. 3 is a schematic diagram of a 4.5 kb plasmid with γ integrase attachment sites engineered into it. As shown, the attachment sites (attB and attP) are separated by 1 kb, thereby resulting in a 1 kb minicircle after site-specific recombination.
Figure 4:
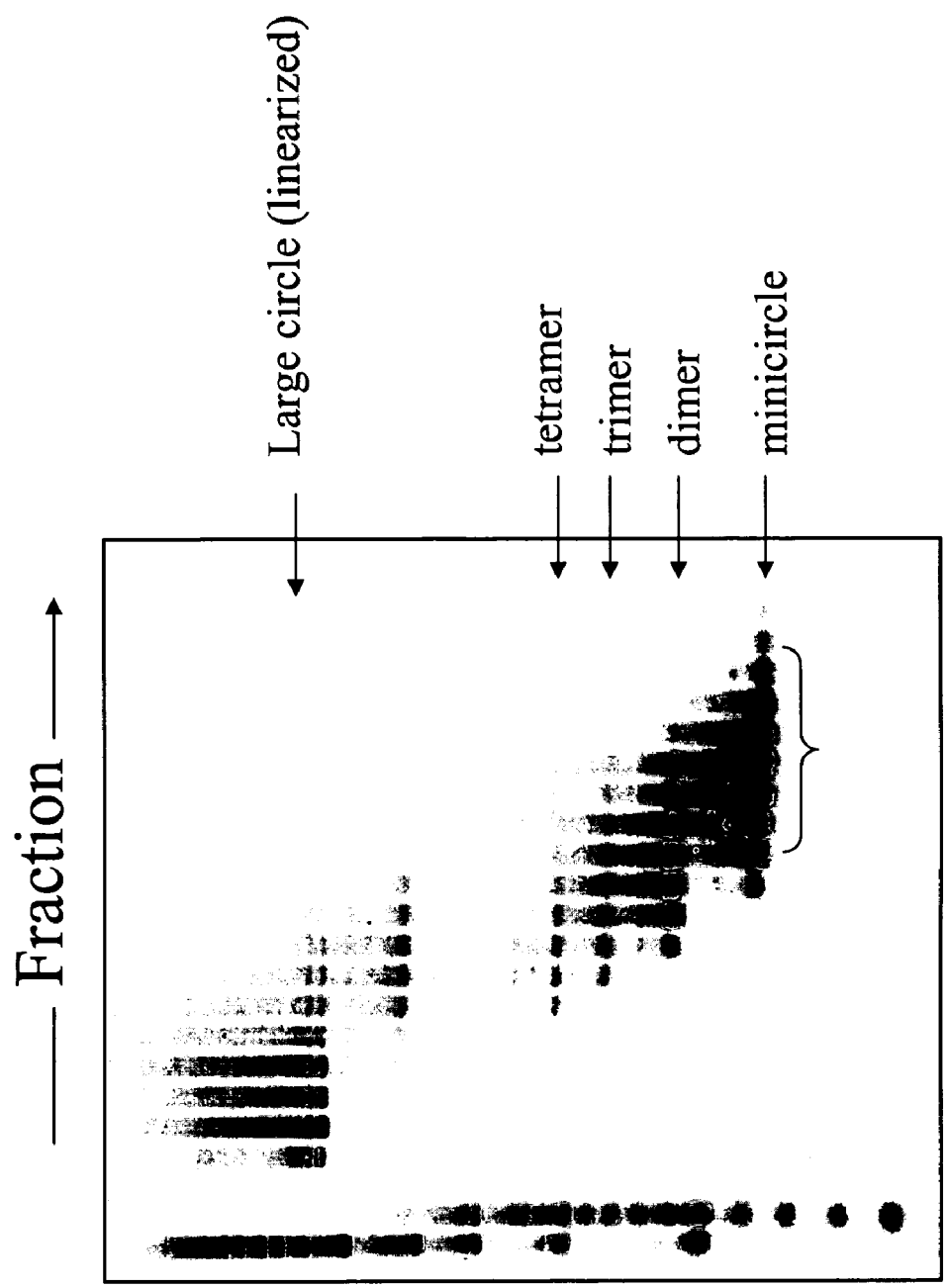
FIG. 4 is a stained image of a gel showing multimeric intermolecular site-specific recombination products. Gel filtration fractions were loaded: linearized large circles elute early, followed by multimeric products of intermolecular recombination, followed by the product minicircles.
Figure 5:
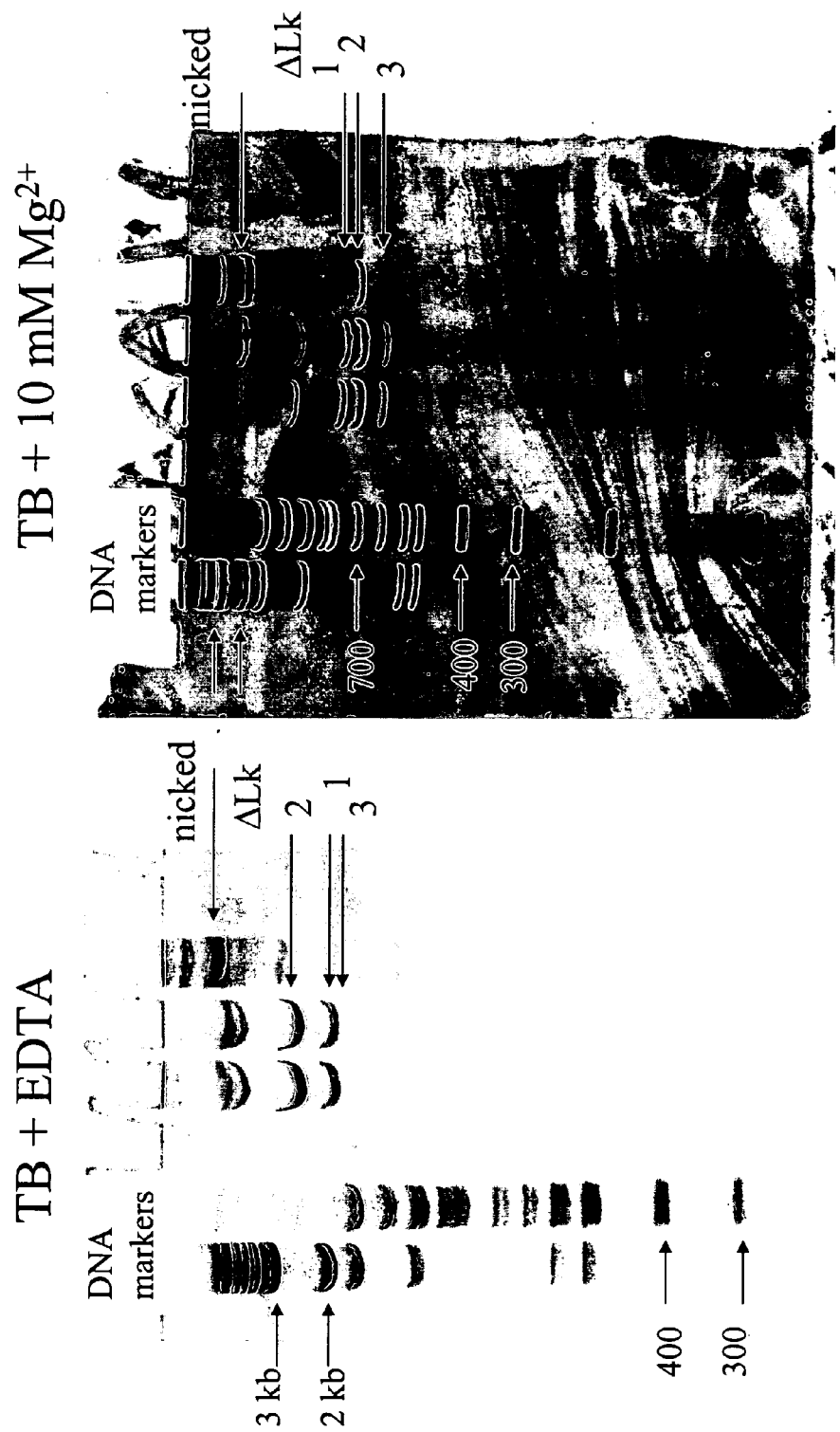
FIG. 5 shows polyacrylamide gels used to separate topoisomers of a 342 bp minicircle. As shown in the gel on the right, the addition of 10 mM $Mg^{2+}$ allows for much clearer separation of topoisomers.

Plasmid patt4.5D has an attB and attP site in the same orientation (FIG. 3). The sites are separated by 1 kb. The plasmid was transformed into LZ54, which expressed γ integrase under the control of a temperature sensitive γ repressor. The LZ54 strain also has a functional topoisomerase IV and a drug-resistant gyrase. The transformed cells are grown to mid log (OD=4) in a fermentor, which enables exponential growth to be maintained at much higher cell densities than in shaker flasks, and shifted to 42° C. to induce expression of integrase. Norfloxacin is added to inhibit the activity of topoisomerase IV, thereby preventing decatenation of the catenated products. The incubation is then shifted back to 30° C. for one hour, as the integrase is not active at 42° C. Other plasmids of varying size have also been engineered, such as, for example, 192 bp, 217 bp, 252 bp, 281 bp, 342 bp, 402 bp and 454 bp. Due to the limitations of γ integrase, 252 bp is the smallest minicircle that has been produced with this particular recombinase, but the use of other site-specific recombination systems would be expected to produce even smaller minicircles—constrained only by the spacer requirements of the particular recombinase. It is possible that as minicircles decrease in size, the energy difference between topoisomers becomes greater and the topoisomer distribution becomes narrower. However, as the size of the space between recombination sites decreases, the prevalence of intermolecular strand transfer products (multimers) increases (FIG. 4).

After site-specific recombination occurs, cellular DNA is extracted by alkaline lysis (cells are resuspended in GLEDT (50 mM glucose, 10 mM EDTA, 25 mM Tris, pH=8) buffer and lysed with an equal volume of 0.2 M NaOH and 1% sodium dodecyl sulfate (SDS)). The SDS-protein complexes that are formed are precipitated with 3M potassium acetate (pH=4) and removed by centrifugation or filtration. High molecular weight RNA is precipitated with LiCl (other salt gradients are known in the art) and low molecular weight RNA is digested with RNase A. Proteinase K is added and plasmid DNA is isolated by QIAGEN-tip 10000™ columns according to manufacturer's instructions. Linearization of the larger DNA circle with BamHI decatenates the products in a way that leaves the minicircle unchanged with respect to Lk. An equal volume of a solution of 10% polyethylene glycol (PEG) 8000, 1.6 M NaCl is added, thereby precipitating the larger, linearized DNA, while the smaller minicircle stays in solution. Following centrifugation the supernatant is extracted with phenol/chloroform and precipitated with ethanol. The resulting DNA pellet, which is mostly minicircle, is resuspended in TE buffer and further purified by gel-filtration (Sephacryl S-500 (Amersham Biosciences)) to isolate the minicircle from any remaining large fragment or RNA. Finally PAGE is used to remove any nicked or multimeric minicircles and also to isolate individual topoisomers.

Analysis of the minicircle topology, prior to the final preparative gel electrophoresis purification step, by gel electrophoresis shows that both 281 base pair (bp) and 342 bp minicircles only adopt two or three detectable topoisomers. In each case one topoisomer is strongly favored. Even without purification by preparative gel electrophoresis up to 90% of the minicircle is present in a single topoisomer. An EcoRV site was engineered into the minicircle sequences enabling restriction enzyme kinetics to be tested on these novel substrates. Other sites can be readily engineered into the minicircles. Initial experiments have focused on the restriction endonuclease EcoRV. Preliminary single-turnover kinetic experiments suggest that the rate of cleavage step is unchanged. For DNA binding studies, a single EcoRV molecule binding to a 342 bp minicircle produces a significant decrease in the electrophoretic mobility. Binding of enzymes to supercoiled DNA, therefore, can be readily studied using simple gel-shift assays. These methods are well known and widely used in the art. These assays will be applicable to other protein-DNA systems. In particular these minicircles are expected to be extremely useful in examining site-specific recombinases and topoisomerases. Furthermore, the milligram quantities now obtainable using our scaled-up preparative method open up the possibility of a wide range of biophysical experiments.

Example 2

Religation of Nicked and Linearized DNA Minicircles

Figure 6:
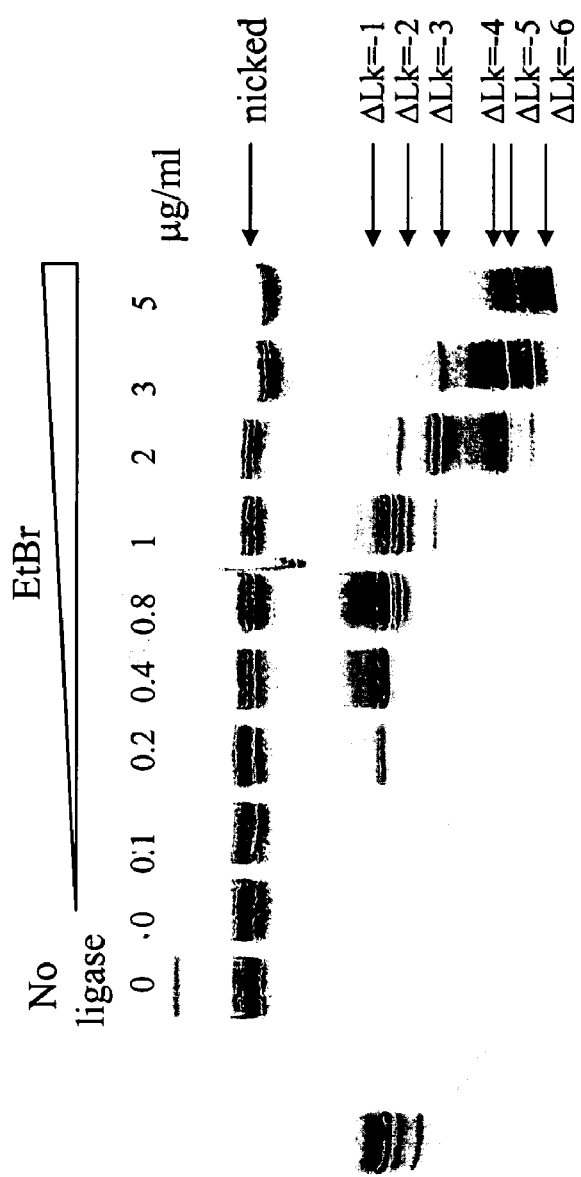
FIG. 6 depicts a polyacrylamide gel demonstrating clear separation of 6 different DNA minicircle topoisomers (ranging in $\Delta Lk$ from −1 to −6). DNA minicircles were generated by ligation of nicked minicircles in the presence of a DNA intercalator, ethidium bromide (EtBr). Note: only monomeric species formed (compare to FIG. 8).
Figure 7:
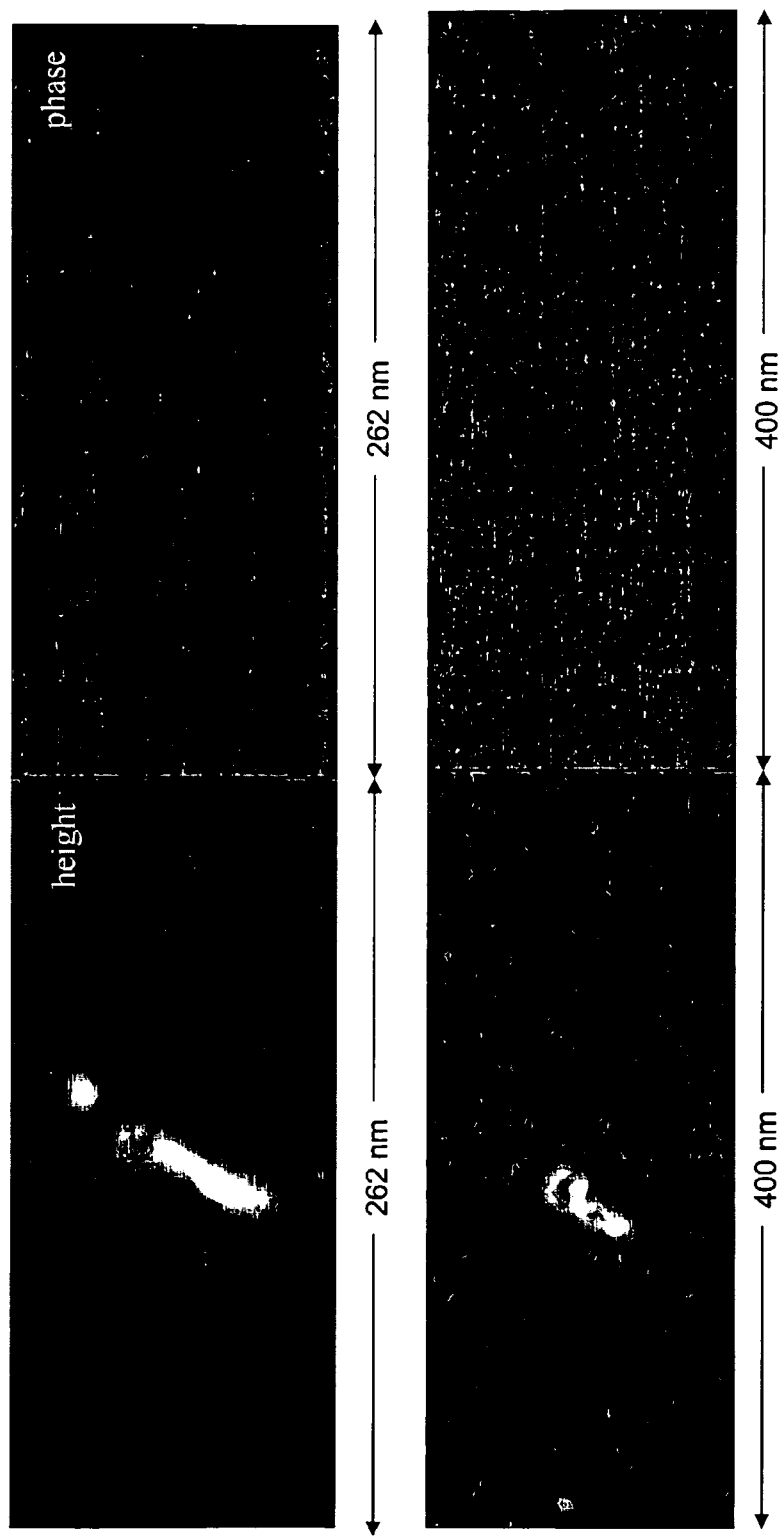
FIG. 7 is an AFM image showing hyper-negatively supercoiled minicircles ($\Delta Lk=-5$) produced from isolated nicked minicircles treated with chemical intercalators.

Nicked minicircles were isolated as described above during the preparative gel electrophoresis purification step, or created by nicking supercoiled DNA minicircles with the nicking endonuclease N.BbvCIB (New England Biolabs; other nicking endonucleases would also be contemplated by the methods of the inventions as well as enzymes with a nicking activity such as, for example, nicking endonucleases and DNaseI). The nicked minicircles were then ligated in the presence of ethidium bromide (EtBr) in various amounts. As shown in FIG. 6, efficient ligation occurs with no detectable intermolecular contaminants. The presence of the DNA intercalator, EtBr, produces hyper-negatively supercoiled minicircles (FIGS. 6 and 7).

Figure 8:
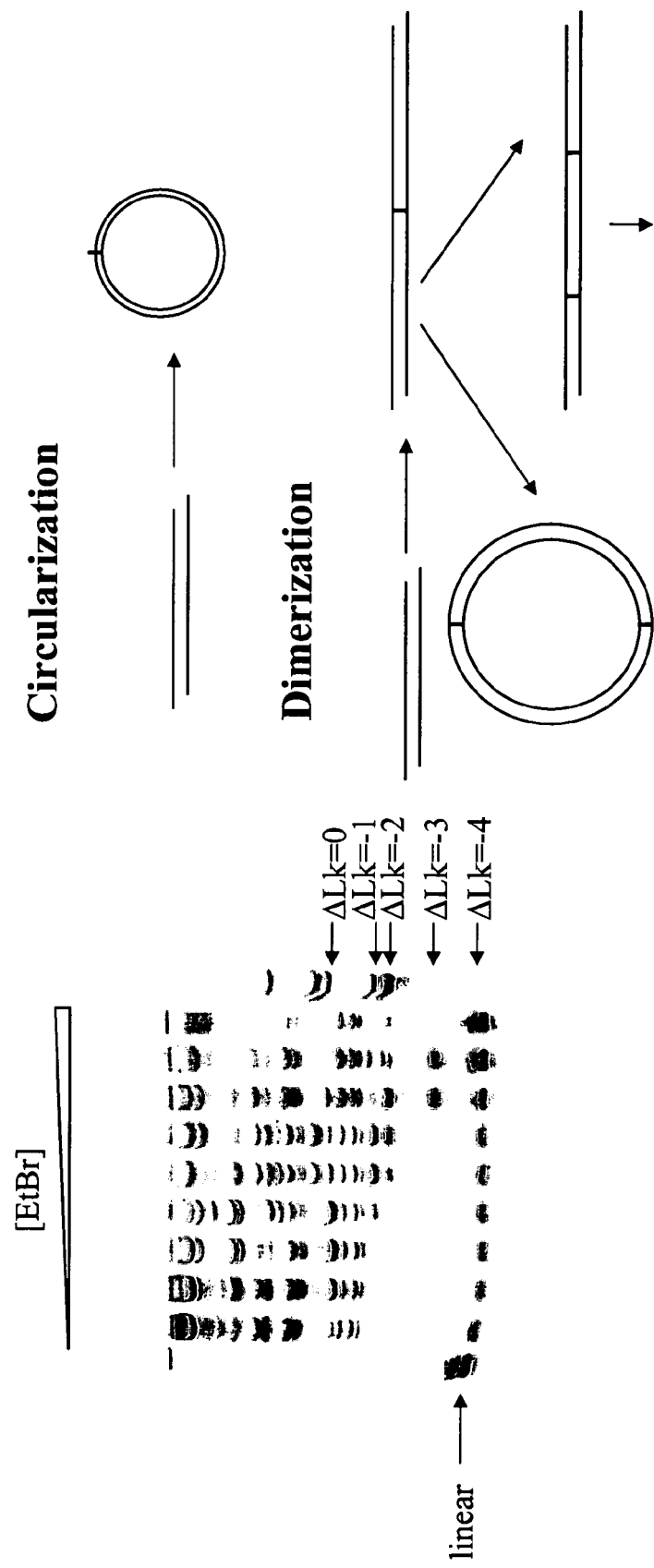
FIG. 8 depicts a polyacrylamide gel showing the separation of supercoiled DNA minicircles. The minicircles were first linearized, and then treated with a chemical intercalator to induce supercoiling during ligation. The appearance of multiple bands is due to multimeric minicircles resulting from intermolecular ligation.

Alternatively, current methods ligate linearized minicircles in the presence of EtBr to produce supercoiled DNA minicircles (FIG. 8). However this must be performed at very low DNA concentrations to prevent the formation of intermolecular contaminants (as shown in FIG. 8). The ligation must be done at DNA concentrations less than 1 microgram per mL. This typically limits yields to less than 1 microgram. The low recovery using current ligation of linear DNA methods clearly suggests a need for a more efficient and higher yield methods such as those described herein.

Figure 9:
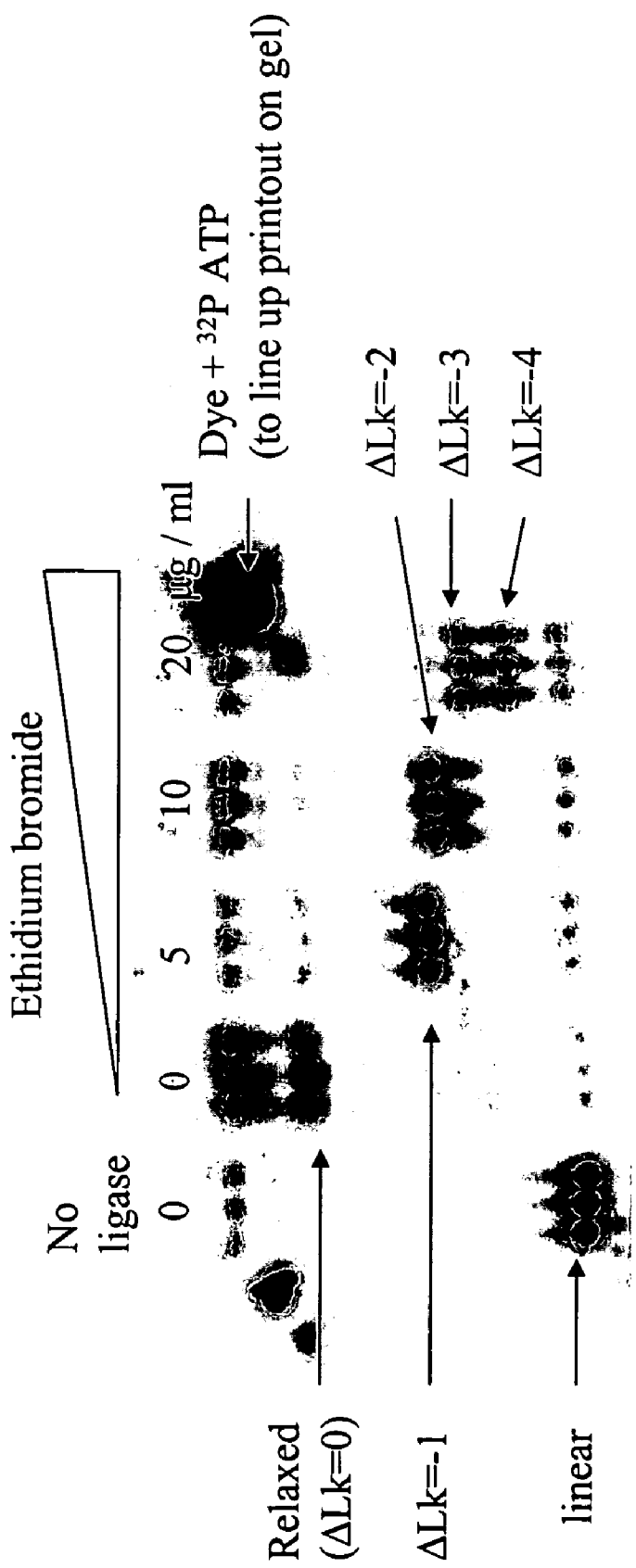
FIG. 9 is an autoradiogram of a gel separating radiolabeled topoisomers of a 342 bp supercoiled DNA minicircle. Linear DNA was radiolabeled, and supercoiling was induced by exposure to a chemical intercalator during ligation.

Ligation of linearized DNA allows for efficient $^{32}$P labeling with T4 polynucleotide kinase. FIG. 9 shows the results of linearizing 1 µg of a 342 bp minicircle with NdeI, followed by dephosphorylation with shrimp alkaline phosphatase and labeling with T4 polynucleotide kinase before overnight ligation in the presence of varying amounts of EtBr. Products were separated and visualized after polyacrylamide gel electrophoresis in the presence of $Ca^{2+}$. Labeled topoisomers are clearly present and largely free of contaminating products (due to the low DNA concentration used in the ligation). This protocol is used if radiolabeled minicircle substrates are required since T4 polynucleotide kinase is inefficient at labeling at a nick.

Figure 10:
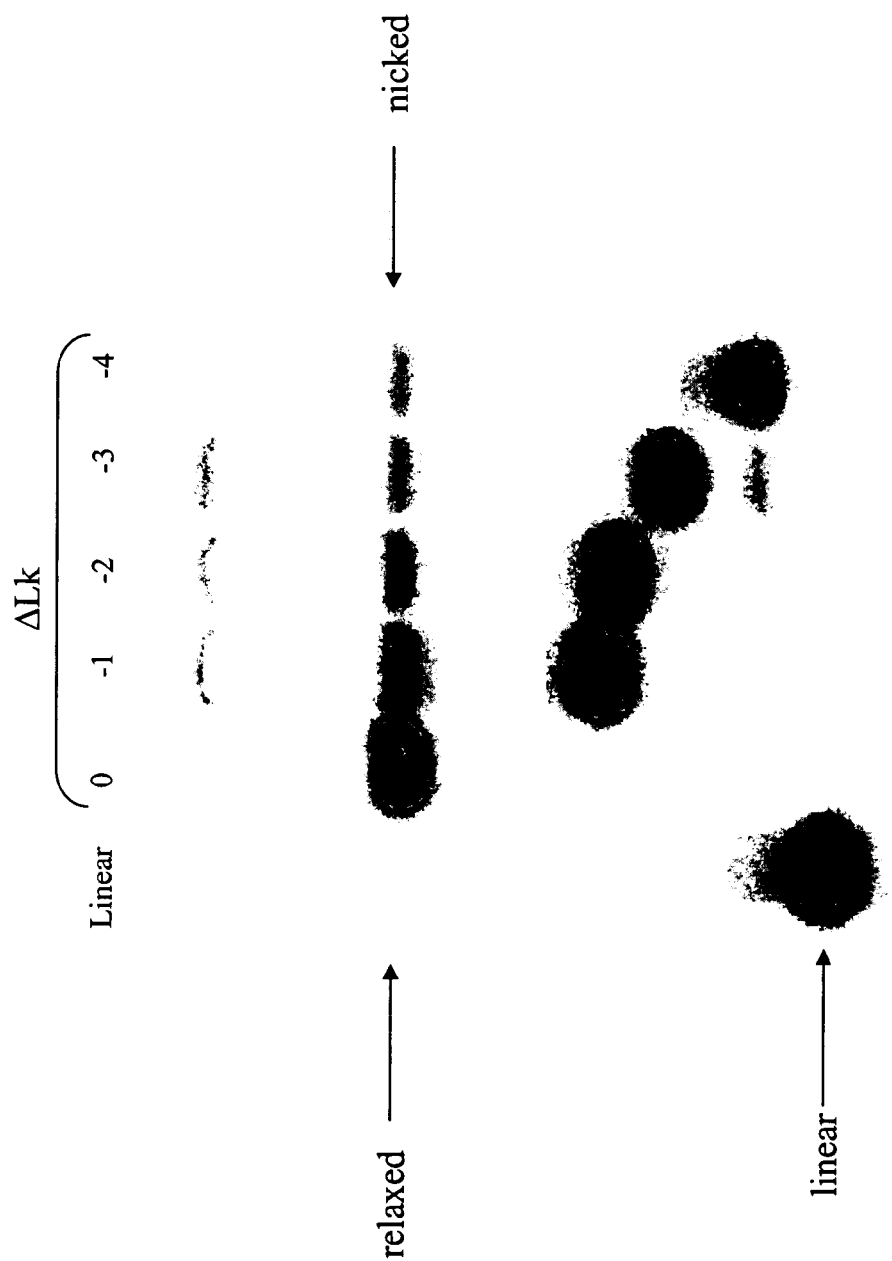
FIG. 10 depicts a gel demonstrating that specific topoisomers of a supercoiled DNA minicircle can be separated. Purified populations of topoisomers obtained after preparative gel electrophoresis are shown.

Single topoisomers can be eluted and purified directly from gel slices by the "crush and soak" elution process. Bands containing particular topoisomers are excised from the gel, physically crushed and allowed to incubate in TE buffer (10 mM Tris-HCl, 1 mM EDTA, pH=8.0). After incubation, the buffer is precipitated with ethanol. Samples of the precipitated eluates are then run on a 5% native agarose gel in the presence of $Ca^{2+}$. Purified topoisomers are shown in FIG. 10.

Example 3

Use of Supercoiled DNA Minicircles as Substrates

Figure 11:
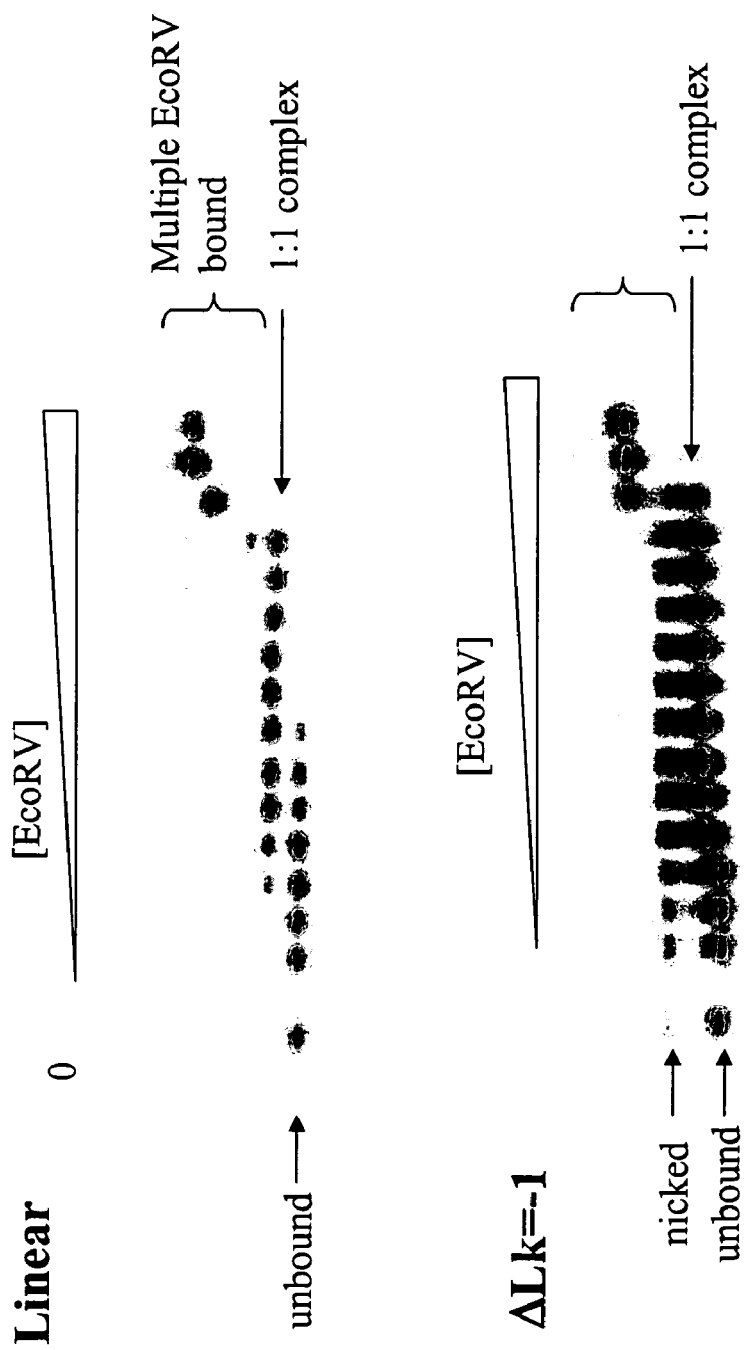
FIG. 11 depicts a gel-shift assay showing protein (EcoRV) binding to a supercoiled DNA minicircle substrate. The substrates were linear (top panel) or circular having a $\Delta Lk$ of −1 (bottom panel).

A 342 bp supercoiled DNA minicircles with an EcoRV binding site engineered into it was used as a substrate for DNA binding studies. Gel-shift assays were performed using either radiolabeled substrates (see Example 2). Alternatively, non-labeled substrates could be used, followed by detection with, for example, SYBR gold staining, however, such detection methods require more substrate. Examples of binding using radiolabeled substrates are shown in FIG. 11. Varying concentrations of EcoRV (8 pM to 1 µM) were incubated with 50 pM of the minicircle substrate. The products were electrophoresed on a 5% native polyacrylamide gel for 2-3 hours at 140V in the presence of 10 mM $Ca^{2+}$. These studies indicate different binding properties of EcoRV to different substrate topoisomers (Linear substrate, $K_D$=36.3 pM; Relaxed substrate, $K_D$=18.8 pM; $\Delta LK$=−1, $K_D$=4.8 pM; $\Delta LK$=−2, $K_D$=4.5 pM; $\Delta LK$=−3, $K_D$=10.6 pM; $\Delta LK$=−4, $K_D$=13.9 pM). The differences in $K_D$ suggest an important topological affect on DNA binding and reinforce the utility of the DNA minicircles described herein as substrates.

Reaction rates were also measured in single-turnover kinetic studies of EcoRV activity. A reaction rate of 3.8/s has been previously reported using a 3.7 kb supercoiled plasmid (Erskine, S. et al., 1997. *Biochemistry*, 36:7567-76). Single-turnover kinetic analysis using the supercoiled 342 bp minicircle resulted in a reaction rate of 2.1/s.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing supercoiled DNA minicircles, comprising:
    a) engineering a plasmid DNA molecule comprising site-specific recombination sites;
    b) transforming the plasmid into a cell suitable for site-specific recombination to occur, under conditions such that topoisomerase IV decatenation activity is inhibited, thereby producing a plurality of catenated DNA circles, wherein at least one of the circles in each catenane is a supercoiled DNA minicircle of less than about 1 kb in size;
    c) decatenating the catenated site-specific recombination products, thereby releasing the supercoiled DNA minicircles from the catenanes; and
    d) isolating the supercoiled DNA minicircles.

2. The method of claim 1, wherein the catenated site-specific recombination products are decatenated by a site-specific endonuclease that does not cleave the supercoiled DNA minicircles.

3. The method of claim 1, wherein nicked minicircles are also produced, and wherein the supercoiled DNA minicircles are separated from the nicked DNA minicircles.

4. The method of claim 1, wherein the site-specific recombination sites are selected from the group consisting of: attB, attP, loxP sites, γδ res sites, FRT sites, hixL, hixR, TN3 res sites, Tn21 res sites, psi sites and cer sites.

5. The method of claim 1, wherein the site-specific recombination utilizes an enzyme selected from the group consisting of: γδ resolvase, Hin recombinase, P1 Cre, yeast 2 micron Flp, Tn3 resolvase, Tn21 resolvase, λ integrase and XerCD.

6. The method of claim 1, wherein the minicircles comprise one or more putative binding sites for one or more proteins of interest.

7. The method of claim 6, wherein the one or more proteins of interest are selected from the group consisting of: topoisomerases, site-specific recombinases, restriction endonucleases, transcription factors, remodeling factors, DNA bending proteins, helicases, polymerases and DNA repair proteins.

8. The method of claim 1, wherein the supercoiled DNA minicircle is attached to a solid support matrix.

9. The method of claim 1, wherein topoisomers of the supercoiled minicircles are separated from each other, thereby producing substantially purified DNA minicircles, wherein the DNA minicircles have the same linking number.

10. The method of claim 9, wherein the DNA minicircles have a $\Delta Lk$ of between about +6 to about −6.

11. The method of claim 10, wherein the DNA minicircles have a $\Delta Lk$ of between about −1 to about −6.

12. The method of claim 1, wherein the site-specific recombination sites are separated by about 100 base pairs to about 1000 base pairs.

13. The method of claim 12, wherein the site-specific recombination sites are separated by about 342 base pairs.

14. A method for producing a population of supercoiled DNA minicircles
    a) engineering a plasmid DNA molecule comprising site-specific recombination sites;
    b) transforming the plasmid into a cell suitable for site-specific recombination to occur, under conditions such that topoisomerase IV decatenation activity is inhibited, thereby producing a plurality of catenated DNA circles, wherein at least one of the circles in each catenane is a supercoiled DNA minicircle of less than about 1 kb in size;
    c) recovering the supercoiled DNA minicircles from the cell;
    d) treating the supercoiled DNA minicircles with an enzyme that introduces nicks into the DNA minicircle; and
    e) ligating the nicked minicircle in the presence of a DNA intercalator that introduces supercoils,
        thereby producing a population of supercoiled DNA minicircles.

15. The method of claim 14, wherein the enzyme that introduces nicks into the DNA minicircle is a nicking endonuclease.

16. The method of claim 14, wherein the DNA intercalator is ethidium bromide.

* * * * *